United States Patent
Burke et al.

(10) Patent No.: US 8,197,506 B2
(45) Date of Patent: Jun. 12, 2012

(54) WOUND CLOSING DEVICE

(76) Inventors: Kenneth Burke, Ivoryton, CT (US); Gary Baier, Ivoryton, CT (US)

( * ) Notice: Subject to any disclaimer, the term of this patent is extended or adjusted under 35 U.S.C. 154(b) by 1122 days.

(21) Appl. No.: 11/855,230

(22) Filed: Sep. 14, 2007

(65) Prior Publication Data

US 2011/0022082 A1    Jan. 27, 2011

(51) Int. Cl.
*A61B 17/08* (2006.01)

(52) U.S. Cl. ......... 606/215; 606/210; 606/211; 606/214

(58) Field of Classification Search ............... 606/151, 606/205, 210, 213–220; 602/43, 48, 54, 602/57, 58, 60, 69; 294/100, 99.2
See application file for complete search history.

(56) References Cited

U.S. PATENT DOCUMENTS

| | | | |
|---|---|---|---|
| 572,564 A * | 12/1896 | Owen | 294/100 |
| 2,371,978 A * | 3/1945 | Perham | 606/216 |
| 4,727,876 A | 3/1988 | Porat et al. | |
| 5,019,091 A | 5/1991 | Porat et al. | |
| 5,259,835 A | 11/1993 | Clark et al. | |
| 5,263,973 A * | 11/1993 | Cook | 606/215 |
| 5,445,597 A | 8/1995 | Clark et al. | |
| 5,514,148 A | 5/1996 | Smith, III | |
| 5,611,794 A | 3/1997 | Sauer et al. | |
| 5,972,021 A | 10/1999 | Huttner et al. | |
| 6,042,599 A | 3/2000 | Huttner et al. | |
| 6,329,564 B1 | 12/2001 | Lebner | |
| 6,410,818 B1 | 6/2002 | Oyaski | |
| 6,822,133 B2 | 11/2004 | Lebner | |
| D500,085 S | 12/2004 | Cotter et al. | |
| 6,831,205 B2 | 12/2004 | Lebner | |
| 6,942,683 B2 | 9/2005 | Dunshee | |
| 7,122,712 B2 | 10/2006 | Lutri et al. | |
| 2005/0070927 A1 | 3/2005 | Feinberg | |
| 2006/0190033 A1* | 8/2006 | Molloy | 606/205 |
| 2006/0200198 A1* | 9/2006 | Riskin et al. | 606/215 |
| 2006/0241691 A1* | 10/2006 | Wilk | 606/215 |
| 2007/0083228 A1* | 4/2007 | Visinoni et al. | 606/210 |
| 2008/0262540 A1 | 10/2008 | Bangera et al. | |
| 2008/0262543 A1 | 10/2008 | Bangera et al. | |

FOREIGN PATENT DOCUMENTS

JP            05103792      *    4/1993

* cited by examiner

*Primary Examiner* — Tuan Nguyen

(74) *Attorney, Agent, or Firm* — Wiggin and Dana LLP

(57) ABSTRACT

A wound (50) is closed using a first adhesive shoe (10) adhesively affixed adjacent to a first edge (51) of the wound, a second adhesive shoe (20) adhesively affixed adjacent to a second opposite edge (52) of the wound, a forceps device (100) comprising a first leg (101) adapted to couple with the first adhesive shoe and a second leg (102) adapted to couple with the second adhesive shoe; and a locking mechanism (150) adapted to draw the first and second forcep legs together and hold legs in the desired closed position after they are drawn together.

21 Claims, 3 Drawing Sheets

WOUND CLOSING DEVICE

BACKGROUND OF THE INVENTION

1. Technical Field

The present invention relates to an apparatus and method for closing a skin wound and more specifically to the art of using tissue glue in combination with tissue approximation forceps to glue wound edges together.

2. Background Art

In recent years, tissue adhesives such as the cyanoacrylates have become widely used for closing skin wounds, both those caused by trauma and those made as surgical incisions. In many cases, the use of tissue adhesives instead of skin sutures or staples allows wounds to be closed without the need for injecting local anesthetic into a wound, thereby expediting the procedure and sparing the patient the pain of an injection.

When a wound is closed using sutures, the process of placing the sutures and tying the associated knots brings the wound edges into proper alignment at the same time that it closes the wound and secures that alignment. Thus it is not necessary to hold the wound edges together during suturing.

When tissue adhesives are used appropriately, they yield cosmetic results typically better than the results achieved using sutures. The chief difficulty with using adhesives to close a wound is that the edges of the wound must be brought into alignment and held there as the liquid adhesive is applied. Unlike sutures, the wound edges must be held and kept in alignment while the adhesive cures. To assist in the process of keeping the wound edges aligned while the adhesive cures, there have been attempts to use prior art tissue forceps. However prior art forceps are not well suited to this task.

Prior art tissue forceps come in a variety of types, each with various tissue mating surfaces adapted for the purpose of grasping the tissue adjacent the edges of a wound in a secure manner. These mating surfaces give only a limited degree of control over the wound edges. Prior art forceps indent the skin and evert the wound edges during closure. This is most desirable for suturing a wound because the edges eventually flatten and give a cosmetically acceptable result. However it is not desireable for wound closure when using a tissue adhesive material in place of sutures.

Prior art forceps also require that one of the treating surgeon's hands be used to secure the forceps in position during the wound closure procedure due to the fact that the forceps will not remain on the skin if one hand does not remain on the forceps. Such limitations in the prior art therefore did not allow the use of two hands to stitch or apply the tissue glue. It is more desirable if the surgeon has his second hand available. The surgeon could then use that second hand to steady the patient rather than keeping it on the forceps in order to keep the wound edges together.

Also In the prior art, if the patient moves then the forceps will move and the wound edges will not maintain registration. When the forceps slip out of position, the wound may open and allow tissue glue to enter the wound. If such forceps were capable of remaining attached to the skin in the closed position, then they would also be free to move with the patient's movement without a loss of wound edge closure.

To solve the aforementioned problems associated with wound closure, the present invention is a unique system for simple and reliable closing of the edges of a wound allowing for optimal application of tissue glue.

The new and improved tissue forceps, according to the present invention, have independent and detachable tissue mating surfaces which adhesively engage the skin adjacent to a wound in a manner which approximates the wound edges. The forceps may also include a locking mechanism which, in many cases, allows the operator to let go of the forceps once the wound edges have been positioned, thereby freeing up one hand.

SUMMARY OF THE INVENTION

The following summary of the invention is provided to facilitate an understanding of some of the innovative features unique to the present invention. A full appreciation of the various aspects of the invention can only be gained by taking the entire specification, claims, drawings, and abstract as a whole.

The present invention is directed to improved wound closure using a forceps device, such as tissue approximation forceps, with detachable adhesive shoes that are adhesively affixed to the edges of the wound. The present invention can be used in combination preferably with applied tissue glue.

According to a first aspect, in which specially adapted bandages are used as the adhesive shoes, the present invention provides a wound closure system comprising a first bandage with an open pocket portion, a second bandage with an open pocket portion, a forceps device, and a locking mechanism. The first bandage is adhesively adjacent to a first longitudinal edge of the wound, with its open pocket portion facing away from the wound. The second bandage is adhesively affixed adjacent to a second longitudinal edge of the wound, with its open pocket portion facing away from the wound. The forceps device includes a first leg adapted to fit within the open pocket portion of the first bandage and a second leg adapted to fit within the open pocket portion of the second bandage. The locking mechanism is adapted to hold the first and second legs in position when they are drawn together by closing the forceps device.

In a further embodiment, tissue glue is applied directly to the edges of the wound when they are drawn together and locked into position.

According to a second aspect, the present invention provides a wound closure system comprising a first adhesive shoe adhesively affixed adjacent to a first longitudinal edge of the wound, a second adhesive shoe adhesively affixed adjacent to a second longitudinal edge of the wound, a forceps device comprising a first leg adapted to couple with the first adhesive shoe and a second leg adapted to couple with the second adhesive shoe; and a locking mechanism adapted to hold the first and second legs in position when they are drawn together by closing the forceps device.

According to a third aspect, the present invention provides a method for closing a wound using a forceps device and tissue glue including the steps of: affixing a first adhesive shoe adjacent to a first longitudinal edge of the wound, affixing a second adhesive shoe adjacent to a second longitudinal edge of the wound, coupling a first leg of said forceps device to said first adhesive shoe, coupling a second leg of said forceps device to said second adhesive shoe, closing the forceps device, thereby drawing the first and second longitudinal edges of said wound substantially together, locking the forceps device such that legs thereof remain fixed in position thereby holding the edges of said wound substantially together, applying tissue glue directly to the edges of said wound, waiting a predetermined period of time for said tissue glue to set, unlocking said forceps device, and decoupling the legs of said forceps device from said first and second adhesive shoes to complete the closing of said wound.

The present invention seeks to overcome or at least ameliorate one or more of several problems with wound closure when using tissue adhesive, including but not limited to unsatisfactory results yielded by using prior art forceps. The present invention frees both of the surgeon's hands during a wound closure procedure so that he will be free to use two hands to apply tissue glue (or sutures, staples or other method, if desired) to join the wound edges together.

When tissue adhesives are used to close a wound, the edges of the wound must be brought into alignment and held there as the adhesive is applied and for long enough for the adhesive to set. With commonly used adhesives such as cyanoacrylates, the wound edges must be held tightly enough together to keep the adhesive from flowing into the wound, as the presence of the adhesive in the wound is injurious to the tissue. Achieving correct alignment of wound edges is important, as misaligned wound edges can result in a poorly formed and unsightly scar. Often, bringing wound edges into alignment is made much more difficult when the patient, who may be a young child, is unable to cooperate with the procedure.

The most common method for bringing wound edges into alignment for application of tissue adhesive is the use of fingers. The user places gloved fingers of one hand on either side of the wound and squeezes the edges together. This method is limited by the amount of friction obtainable between the medical operator's gloved hand and the patient's skin. The medical operator's fingers must also apply downward pressure to either side of the wound in order to obtain friction, and this pressure can be painful for the patient. It is easily possible for the adhesive to flow to the medical operator's glove, sticking the glove to the patient's skin.

In another method, standard surgical forceps are placed with one leg of the forceps on either side of the wound, the forceps pressed down and squeezed together. However, there is typically not enough friction available to bring the wound edges together, and the downward pressure applied can be painful to the patient. Finally, as with the use of fingers, the forceps like the glove can inadvertently be glued to the patient's skin.

In a third method, specially adapted forceps whose tips have flat surfaces with one or more pointed protrusions for increasing friction can be used to approximate the wound edges. With this method, the protrusions can cause pain as they are pressed into the skin, and the forceps can slip out of position during the application of the adhesive. All of the above methods can often be defeated by the movements of an uncooperative patient such as a young child.

In each of the above present methods, it is important to recognize that while the tissue glue sets, the medical practitioner must maintain the wound edge alignment by holding the wound edges together. The present invention can eliminate this problem because the adhesive shoes allow the forceps to remain properly positioned on the skin surface even without the aid of the medical practitioner's hand holding them in place. The locking mechanism of the forceps holds the wound edges aligned. Thus the combination of the adhesive shoes and locking mechanism gives the medical practitioner the option to remove their hands from the forceps.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

BRIEF DESCRIPTION OF DRAWINGS

The accompanying figures further illustrate the present invention.

BRIEF DESCRIPTION OF THE SEVERAL VIEWS OF THE DRAWING

Figure 1:
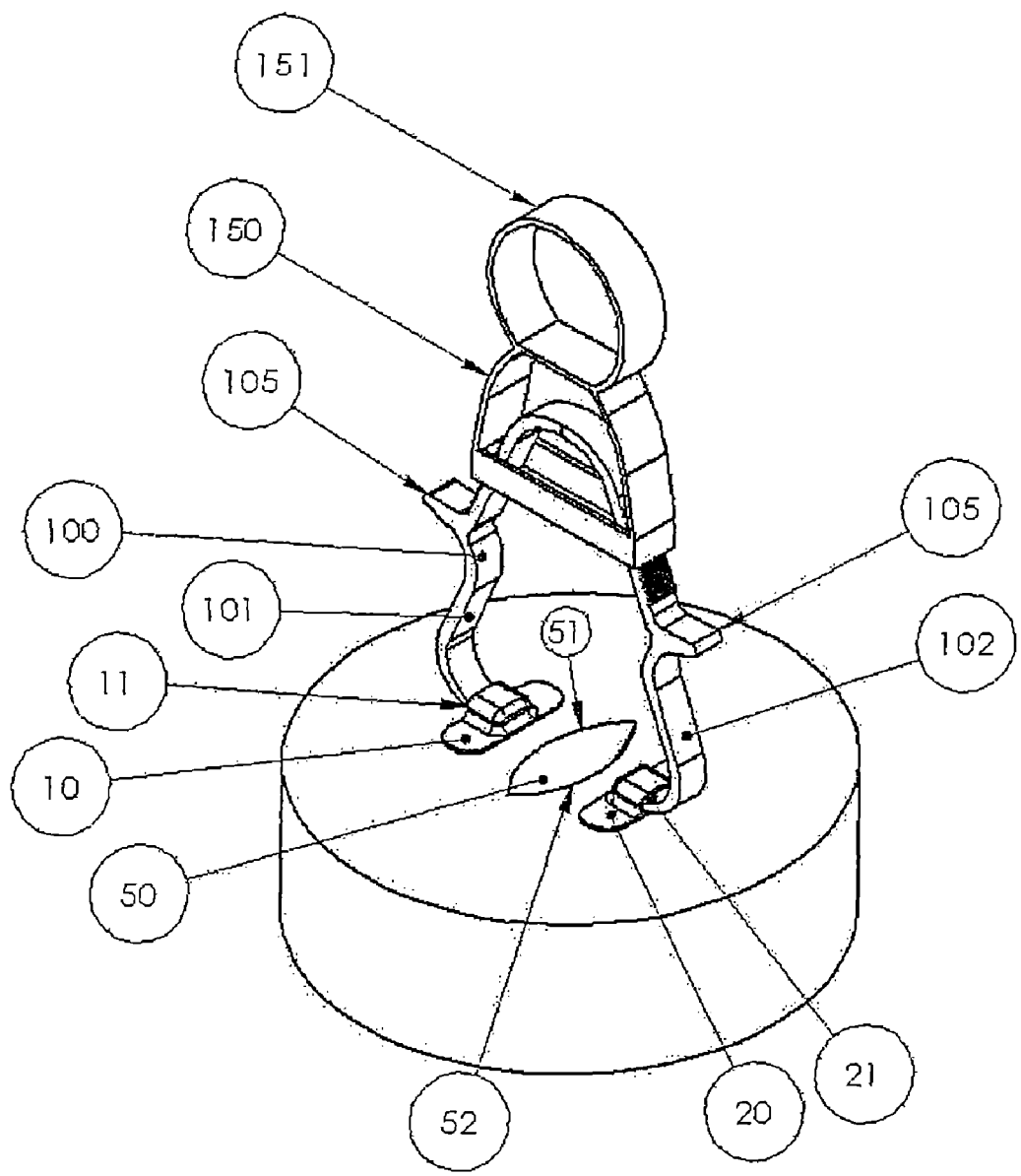

FIG. 1 shows a wound closure system that uses bandages with open pocket portions in accordance with a first illustrative embodiment of our invention.

Figure 2:
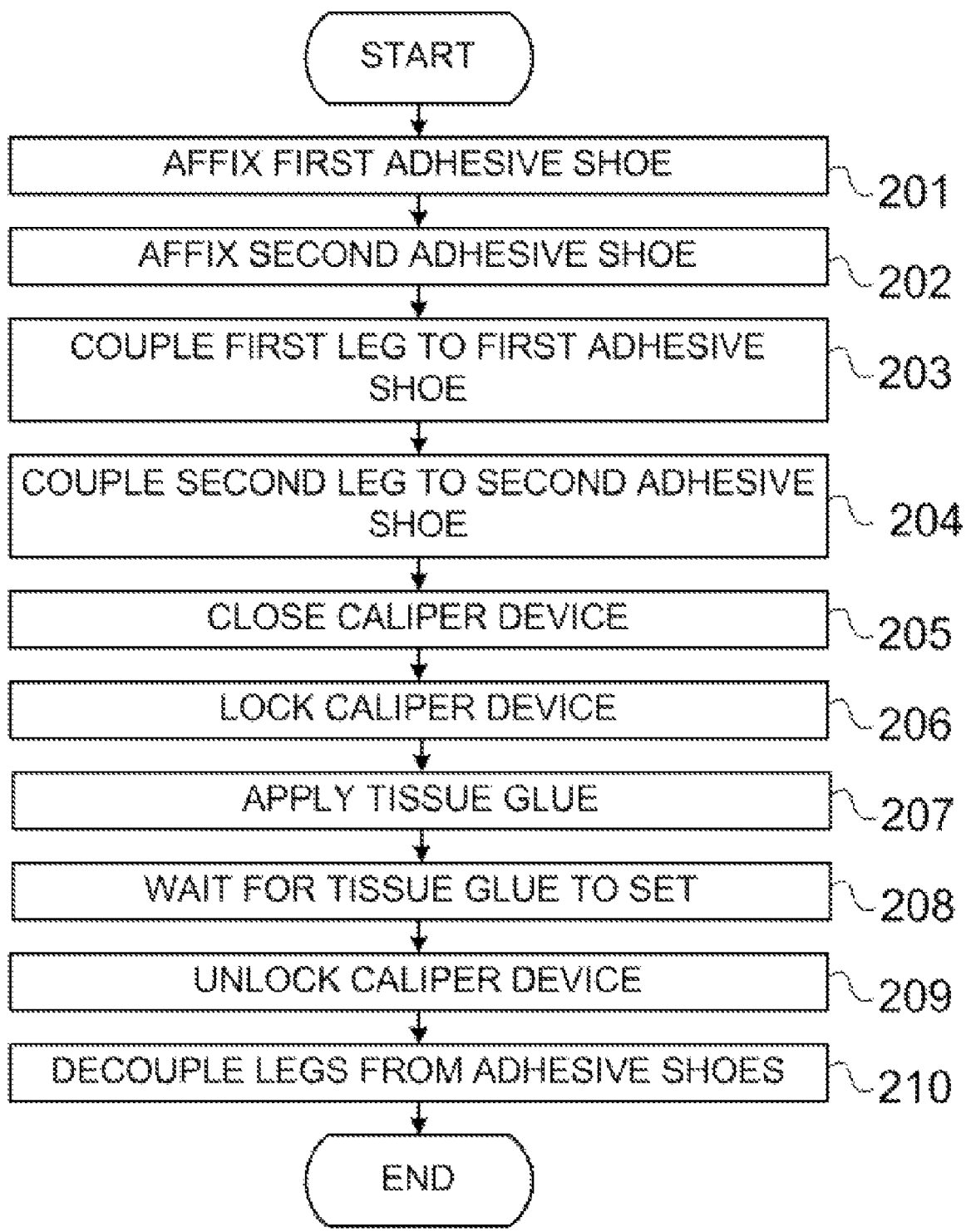

FIG. 2 depicts an illustrative method of closing a wound in accordance with our invention.

Figure 3:
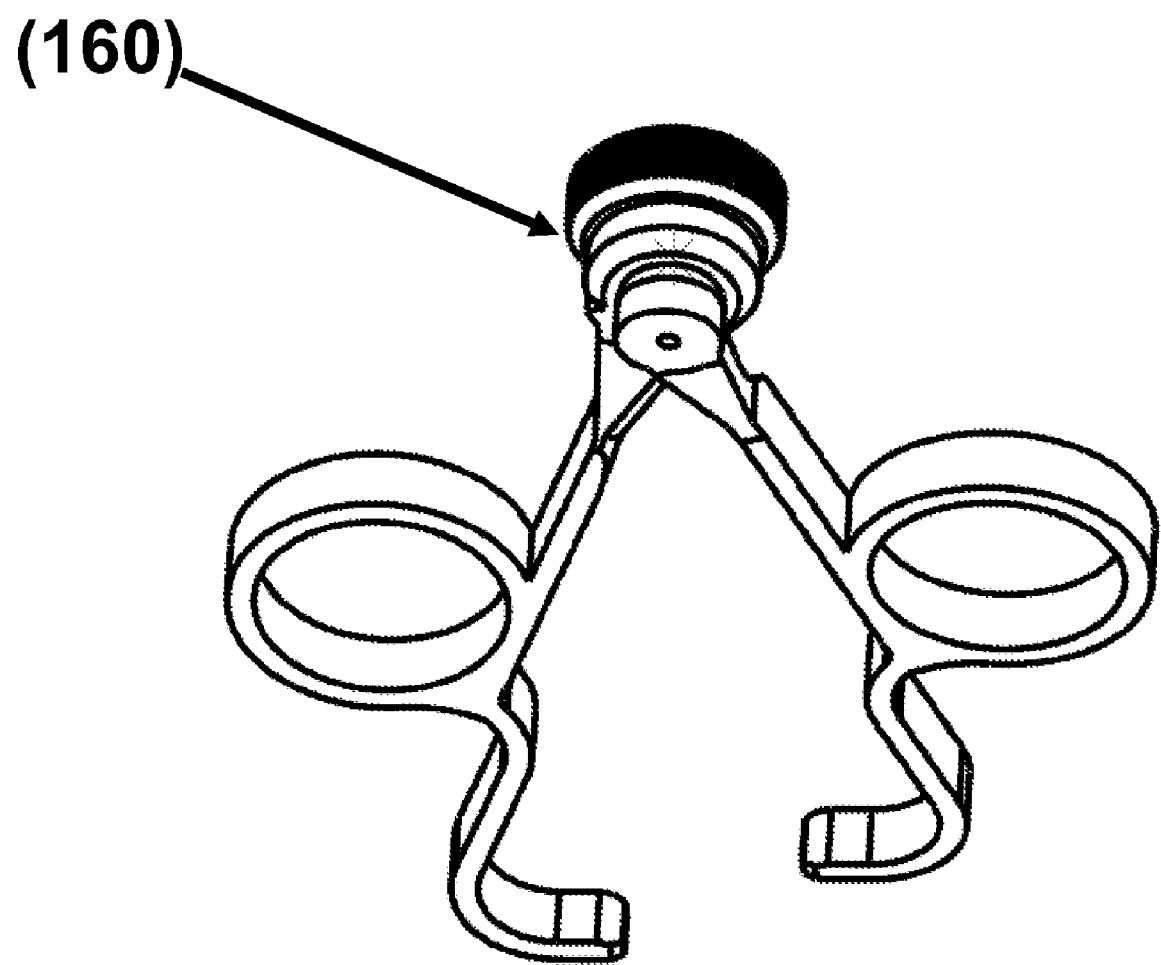

FIG. 3 depicts a wound closure system in which a forceps device includes a pivot where the first and second forceps legs connect, in accordance with an alternative embodiment.

LIST OF REFERENCE NUMBERS FOR THE MAJOR ELEMENTS IN THE DRAWING

The following is a list of the major elements in the drawings in numerical order.
10 first adhesive shoe (e.g. specially adapted bandage)
11 open pocket (of bandage 10)
20 second adhesive shoe (e.g. bandage)
21 open pocket (of bandage 20)
50 wound
51 first longitudinal edge (of wound 50)
52 second longitudinal edge (of wound 50)
100 forceps device
101 first leg (of forceps device 100)
102 second leg (of forceps device 100) 105 wings
150 locking mechanism
151 push top (part of locking mechanism 150)
160 pivot
201 (step of) affixing a first adhesive shoe
202 (step of) affixing a second adhesive shoe
203 (step of) coupling a first forceps leg to the first adhesive shoe
204 (step of) coupling a second forceps leg to the second adhesive shoe
205 (step of) closing the forceps device
206 (step of) locking the forceps device
207 (step of) applying tissue glue
208 (step of) waiting for tissue glue to dry
209 (step of) unlocking the forceps device
210 (step of) decoupling the legs of the forceps device

DESCRIPTION OF THE INVENTION

The present invention is designed for use within a medical treatment environment for the purpose of closing skin wounds in place of more traditional stitches.

MODE(S) FOR CARRYING OUT THE INVENTION

Refer first to FIG. 1, which shows a first illustrative embodiment of the present invention. A patient has an open wound 50 that a surgeon is working to close with a forceps device 100, such as tissue approximation forceps. A left adhesive shoe, such as a first bandage 10, is applied to the patient's skin adjacent to a first longitudinal edge 51 of wound 50. A right adhesive shoe, such as a second bandage 20, is applied to the patient's skin adjacent to a second opposing longitudinal edge 52 of wound 50. Next, the forceps legs 101 and 102 are slipped into the respective left and right shoes, such as open pocket portions 11 and 21 of the first and second bandages 10 and 20. The forceps has sufficient stiffness to cause eversion of the wound edges when they are brought together by the closing of the forceps.

Other embodiments of the present invention use different configurations in place of adhesive shoes for attaching the forceps to the skin surface, such as detachable portion of the forceps legs or even magnets that are affixed to edges of the wound. Another embodiment of the invention uses a weak adhesive applied directly to the legs of the forceps. In this embodiment, the ends of the forceps adhere directly to the skin surface, without the use of adhesive shoes. The adhesive is just strong enough to allow the forceps to control the wound edges but is weak enough to allow the legs of the forceps to be removed easily from the skin surface after the tissue glue has been applied and has cured.

In yet another embodiment, the adhesive shoes are slipped onto the respective left and right forceps legs and then the forceps are pressed across the injury area to straddle the wound 50. The adhesive shoes attach to the skin when the forceps are pressed down onto the skin. This embodiment does not require the surgeon to press down hard on the wound 50, thus avoiding a source of pain and giving much greater control over the skin.

The forceps legs 101 and 102 can then be drawn together by the surgeon to bring the edges 51 and 52 of the wound 50 together into proper registration. In new inventive forceps, the surgeon's fingers provide the force needed to close the jaws of the forceps. In an embodiment, the forceps device further includes a mechanical stop to prevent the forceps legs from being drawn too close together. The new improved forceps come in contact with only the skin surface such that there is no actual clamping of any tissue. The closing of the jaws of our forceps is done without the mechanism grasping the skin. Advantageously, our invention does not have any protrusions that poke into the skin of the patient, avoiding this source of pain.

A locking mechanism 150, such as a collar, serves to maintain a position of the closure of the forceps that has already been attained. The locking mechanism may have a push top portion 151; as shown in FIG. 1, the shape of the push top portion may be at least a portion of a circle configured to accommodate the surgeon's thumb or finger as the surgeon pushes downward or pulls upward on the locking mechanism. Advantageously, once the forceps are locked in place with the wound edges 51 and 52 in registration, the forceps are retained "hands free" on the patient. In certain embodiments, wings 105 are mounted on the legs of the forceps device to allow the surgeon's fingers or thumb(s) to resist the force of the locking device and to allow the surgeon added degree of control in applying a lifting movement to one or both wound edges.

The surgeon is then free to use both hands during the remainder of the wound closure procedure. Advantageously, the use of adhesive shoes allows a greater ability to position the wound edges 51 and 52 into a desired registration of tissue movement because such adhesive shoes allow both lateral movement and a vertical lifting movement to be applied to one or both of the wound edges, which can facilitate better positioning of some wound edges. Certain embodiments of the present invention incorporate an additional degree of freedom in the forceps device to allow a small additional amount of longitudinal movement perpendicular to the direction of closing the wound.

Finally, tissue glue is applied to hold the edges 51 and 52 of the wound 50 together. Note that the inventive forceps can be used not only with tissue glue but also with conventional wound closure methods, such as staples, sutures or stitches, since they help keep the wound edges in position and keep both of the treating surgeon's hands free.

The invention provides much greater control in manipulating the wound edges. It also keeps the space over the wound open, not blocked, such as by a covering pad. Advantageously, this allows for better visualization of the wound, allows the wound to be blotted dry after the edges have been positioned, and allows the adhesive to be applied directly to the wound surface, without the use of a pad.

Refer now to FIG. 2 which illustrates a method of closing a wound in accordance with an illustrative embodiment of the present invention. First, the surgeons affixes (step 201) a first adhesive shoe adjacent to a first longitudinal edge 51 of the wound 50, as shown in FIG. 1. Next, the surgeon affixes (step 202) a second adhesive shoe adjacent to a first longitudinal edge 52 of the wound 50, as shown in FIG. 1.

The surgeon couples (step 203) a first leg of a forceps device, such as forceps, to the first adhesive shoe and then couples coupling (step 204) a second leg of said forceps device to the second adhesive shoe. As noted above, in alternate embodiments, the adhesive shoe can be first coupled to the legs of the forceps and then pressed onto the patient's skin. Also, the present invention contemplates several coupling schemes, including, but not limited to pocket portions of bandages, detachable portions of forceps legs, rigid adhesive shoes and adhesive magnets.

The surgeon closes (step 205) the forceps device, such as forceps, and thereby draws the first and second longitudinal edges of said wound substantially together. Next, the surgeon locks (step 206) the forceps device such that legs thereof remain fixed in position thereby holding the edges of said wound substantially together and applies (step 207) tissue glue directly to the edges of the wound Finally, after waiting (step 208) a predetermined period of time for the tissue glue to set, the surgeon unlocks (step 209) the forceps device; and decouples (step 209) the legs of the forceps device from the first and second adhesive shoes to complete the closing of the wound.

In the present inventive forceps, the medical practitioner's fingers provide the force needed to close the jaws of the forceps. The collar only serves to maintain a position of the jaws that has already been attained.

With the present invention there is no actual clamping of any tissue. The closing of the jaws of the forceps is done without the forceps grasping or pinching the skin.

Alternate Embodiments

Alternate embodiments may be devised without departing from the spirit or the scope of the invention.

By way of example, rather than affixing the adhesive shoes to the respective edges of the wound and then coupling one of each of the legs of the forceps to an adhesive shoe, the legs can first be coupled to the adhesive shoes prior the adhesive shoes being affixed to the edges of the wound.

Yet another embodiment may incorporate an additional degree of freedom of the jaws to allow a small amount of lateral movement. By providing a pivot (160) where the first and second forceps legs connect, each individual leg may be rotated to align with opposing wound edges that are not parallel. The locking mechanism (150) is replaced with locking nut or thumbwheel attached to the pivot point which allows holding the forceps in the desired closed position.

The pivot could be a swivel joint, a ball joint or other similar assembly well known in the art that provides the ability for each forceps leg to move in a rotational fashion in relationship to the opposite leg. FIG. 3 shows the alternative forceps with the flexible pivot (160).

It would be apparent to one skilled in the art to alter the sequence of steps in other similar fashions without altering the results achieved with the invention.

What is claimed is:

1. A wound closure system adapted for closing a wound, said wound closure system comprising:
    (a) a first bandage, comprising an open pocket portion thereof, configured to adhesively affix adjacent to a first edge of the wound, said open pocket portion of said first bandage facing away from said wound;
    (b) a second bandage, comprising an open pocket portion thereof, configured to adhesively affix adjacent to a second opposite edge of the wound, said second wound edge opposing said first wound edge and said open pocket portion of said second bandage facing away from said wound, said first bandage and said second bandage separated from each other on opposite sides of the wound;
    (c) a forceps device comprising a first leg adapted to fit within said open pocket portion of said first bandage and a second leg adapted to fit within said open pocket portion of said second bandage;
    (d) the forceps device further includes a locking mechanism adapted to hold said first and second legs in position when they are drawn together by closing said forceps device, thereby approximating the first edge of the wound to the second edge of the wound while the first bandage and the second bandage remain separated from each other without a mechanical connection above the wound other than by said forceps device.

2. The wound closure system according to claim 1, further comprising:
    (a) tissue glue suitable for application directly to the edges of said wound when they are drawn together and held in the closed position.

3. The wound closure system according to claim 1, further comprising:
    (a) stitches suitable for application directly to the edges of said wound when they are drawn together and held in the closed position.

4. The wound closure system according to claim 1, wherein the locking mechanism comprises:
    (a) a collar that fits over said forceps device and is adapted to close said forceps device when downward pressure is applied to said collar;
    (b) a push top mounted on said collar and configured to prevent said collar from being placed upside down on said forceps device; and
    (c) wings mounted on the first and second legs of said forceps device, wherein said wings are configured to allow a surgeon's fingers or thumb to be placed thereunder and thereby resist the force of said downward pressure applied to said collar.

5. The wound closure system according to claim 4, wherein said wings allow the vertical lifting of at least one wound edge.

6. The wound closure system according to claim 4, wherein said push top is integral with said collar, and wherein the shape of said push top is at least a portion of a circle.

7. The wound closure system according to claim 4, wherein said wings are configured to prevent the surgeon's fingers or thumb from sliding up the forceps.

8. The wound closure system according to claim 7, wherein the forceps device has sufficient stiffness to cause eversion of the wound edges when they are brought together by the closing of said forceps device.

9. A wound closure system adapted to closing a wound, said wound closure system comprising:
    (a) a first adhesive shoe having an adhesive on a surface thereof for affixing to a patient's skin and thereby configured to adhesively affix adjacent to a first edge of the wound;
    (b) a second adhesive shoe having an adhesive on a surface thereof for affixing to a patient's skin and thereby configured to adhesively affix adjacent to a second opposite edge of the wound, said first adhesive shoe and said second adhesive shoe separated from each other on opposite sides of the wound;
    (c) a forceps device comprising a first leg adapted to couple with said first adhesive shoe and a second leg adapted to couple with said second adhesive shoe; and
    (d) the forceps device further includes a locking mechanism adapted to hold said first and second legs in position when they are drawn together by closing said forceps device, thereby approximating the first edge of the wound to the second edge of the wound while the first adhesive shoe and the second adhesive shoe remain separated from each other without a mechanical connection above the wound other than by said forceps device.

10. The wound closure system of claim 9 wherein:
    (a) the first leg of said forceps device couples to said first adhesive shoe using a mechanical coupling; and
    (b) the second leg of said forceps device couples to said second adhesive shoe using a mechanical coupling.

11. The wound closure system of claim 9 wherein:
    (a) the first leg of said forceps device couples to said first adhesive shoe using a magnetic coupling; and
    (b) the second leg of said forceps device couples to said second adhesive shoe using a magnetic coupling.

12. The wound closure system of claim 9 wherein:
    (a) the first adhesive shoe comprises a first bandage with an open pocket portion;
    (b) the second adhesive shoe comprises a second bandage with an open pocket portion;
    (c) the first leg of said forceps device couples to said first adhesive shoe by being inserted into the open pocket portion of said first bandage; and
    (d) the second leg of said forceps device couples to said second adhesive shoe by being inserted into the open pocket portion of said second bandage.

13. The wound closure system of claim 12 further comprising: tissue glue suitable for application directly to the edges of said wound when they are drawn together and locked into position.

14. The wound closure system according to claim 1, wherein the first leg and the second leg of the forceps device each have a first end and a second end, the first leg and the second leg are each adapted to fit at the first end thereof within the open pocket portions of the first bandage and the second bandage respectively, and further comprising a pivot connecting the first leg and the second leg of the forceps device at the respective second ends.

15. The wound closure system according to claim 14, wherein said locking mechanism comprises a locking nut or thumbwheel attached to the pivot.

16. The wound closure system according to claim 14, wherein the pivot comprises an assembly permitting rotational movement of each leg of the forceps device with respect to the other leg of the forceps device.

17. The wound closure system according to claim 9, wherein the first leg and the second leg of the forceps device each have a first end and a second end, the first leg and the second leg are each adapted to couple at the first end thereof with the first adhesive shoe and the second adhesive shoe respectively, and further comprising a pivot connecting the first leg and the second leg of the forceps device at the respective second ends.

18. The wound closure system according to claim 17, wherein said locking mechanism comprises a locking nut or thumbwheel attached to the pivot.

19. The wound closure system according to claim 17, wherein the pivot comprises an assembly permitting rotational movement of each leg of the forceps device with respect to the other leg of the forceps device.

20. A wound closure system adapted for closing a wound, said wound closure system comprising:
   (a) a first bandage, comprising an open pocket portion thereof, configured to adhesively affix adjacent to a first edge of the wound, said open pocket portion of said first bandage facing away from said wound;
   (b) a second bandage, comprising an open pocket portion thereof, configured to adhesively affix adjacent to a second opposite edge of the wound, said second wound edge opposing said first wound edge and said open pocket portion of said second bandage facing away from said wound, said first bandage and said second bandage separated from each other on opposite sides of the wound;
   (c) a forceps device comprising a first leg adapted to fit within said open pocket portion of said first bandage and a second leg adapted to fit within said open pocket portion of said second bandage;
   (d) the forceps device further includes a locking mechanism adapted to hold said first and second legs in position when they are drawn together by closing said forceps device, thereby approximating the first edge of the wound to the second edge of the wound while the first bandage and the second bandage remain separated from each other without a mechanical connection above the wound other than by said forceps device, said locking mechanism including a collar that fits over said forceps device and is adapted to close said forceps device when downward pressure is applied to said collar.

21. A wound closure system adapted to closing a wound, said wound closure system comprising:
   (a) a first adhesive shoe having an adhesive on a surface thereof for affixing to a patient's skin and thereby configured to adhesively affix adjacent to a first edge of the wound;
   (b) a second adhesive shoe having an adhesive on a surface thereof for affixing to a patient's skin and thereby configured to adhesively affix adjacent to a second opposite edge of the wound, said first adhesive shoe and said second adhesive shoe separated from each other on opposite sides of the wound;
   (c) a forceps device comprising a first leg adapted to couple with said first adhesive shoe and a second leg adapted to couple with said second adhesive shoe; and
   (d) the forceps device further includes a locking mechanism adapted to hold said first and second legs in position when they are drawn together by closing said forceps device, thereby approximating the first edge of the wound to the second edge of the wound while the first adhesive shoe and the second adhesive shoe remain separated from each other without a mechanical connection above the wound other than by said forceps device, said locking mechanism including a collar that fits over said forceps device and is adapted to close said forceps device when downward pressure is applied to said collar.

* * * * *